(12) United States Patent
Bishop

(10) Patent No.: US 7,115,559 B2
(45) Date of Patent: Oct. 3, 2006

(54) METHOD FOR TREATING COUMARIN-INDUCED HEMORRHAGE

(75) Inventor: Paul D. Bishop, Fall City, WA (US)

(73) Assignee: Zymogenetics Inc., Seattle, WA (US)

( * ) Notice: Subject to any disclaimer, the term of this patent is extended or adjusted under 35 U.S.C. 154(b) by 25 days.

(21) Appl. No.: 10/489,082

(22) PCT Filed: Sep. 10, 2002

(86) PCT No.: PCT/US02/28737

§ 371 (c)(1),
(2), (4) Date: Mar. 5, 2004

(87) PCT Pub. No.: WO03/022305

PCT Pub. Date: Mar. 20, 2003

(65) Prior Publication Data

US 2004/0242480 A1    Dec. 2, 2004

Related U.S. Application Data

(60) Provisional application No. 60/322,231, filed on Sep. 10, 2001.

(51) Int. Cl.
*A61K 38/36*    (2006.01)
*C07K 14/745*    (2006.01)

(52) U.S. Cl. .......................................... 514/2; 530/381

(58) Field of Classification Search ................ None
See application file for complete search history.

(56) References Cited

U.S. PATENT DOCUMENTS

| | | | | |
|---|---|---|---|---|
| 3,458,287 A | * | 7/1969 | Gross et al. | 436/69 |
| 3,931,399 A | * | 1/1976 | Bohn et al. | 530/381 |
| 4,503,039 A | * | 3/1985 | Kotitschke et al. | 424/530 |
| 4,525,341 A | * | 6/1985 | Deihl | 424/43 |
| 4,627,879 A | * | 12/1986 | Rose et al. | 106/124.1 |
| 5,610,147 A | * | 3/1997 | Seelich | 514/21 |
| 5,612,456 A | * | 3/1997 | Bishop et al. | 530/381 |
| 5,710,174 A | * | 1/1998 | West et al. | 514/450 |

OTHER PUBLICATIONS

File HCAPLUS on STN, DN No. 116:15565. Uemura et al. 'Basic Research for Hemostatic Agen, 'GTXIII'. Study for Hemostatic and Thromgenic Ability in in Vivo.' Sitai Zairyo (1991), 9(2), 56-63. Abstract Only, Abstract date Jan. 1992.*

* cited by examiner

*Primary Examiner*—Anish Gupta
(74) *Attorney, Agent, or Firm*—Len S. Smith; Reza Green; Richard Bork

(57) ABSTRACT

Use of factor XIII for treating coumarin-induced hemorrhage or bleeding. The coumarin may be warfarin or dicoumarol. A patient having coumarin-induced bleeding is treated with factor XIII alone or in conjunction with vitamin K.

7 Claims, No Drawings

METHOD FOR TREATING COUMARIN-INDUCED HEMORRHAGE

The present application is a 35 U.S.C. 371 application of PCT/US02/28737 filed Sep. 10, 2002, which claims the benefit of U.S. Provisional Application Ser. No. 60/322,231 filed Sep. 10, 2001, both of which are incorporated by reference herein.

BACKGROUND OF THE INVENTION

Vitamin K controls the formation of prothrombin, factor VII, factor IX, and factor X by acting as a substrate for the enzyme γ-glutamyl carboxylase. This enzyme catalyzes the addition of carbon dioxide to the γ-carbon of protein-bound glutamic acid in the gla regions of the coagulation factors.

Coumarin anticoagulants, which include warfarin and dicumarol (dicoumarol), prevent the reduction of vitamin K epoxides in the liver microsomes and induce a state of vitamin K deficiency. A side effect of such anticoagulants is hemorrhage. If hemorrhage does occur, there is a need for a substance to inhibit the coumarin anticoagulant-induced bleeding.

DESCRIPTION OF THE INVENTION

The present invention fills this need by administering factor XIII to patients afflicted with bleeding due to a coumarin anticoagulant-induced vitamin K deficiency. Factor XIII can be administered alone or in conjunction with cryoprecipitate or fresh frozen plasma, generally two units or plasma. Vitamin K can also be administered at an initial dose of 5 to 10 mg, generally subcutaneously. The administration of factor XIII can be applied prophylactically or at the time of a bleeding episode.

Factor XIII, also known as fibrin-stabilizing factor, circulates in the plasma at a concentration of 20 μg/ml. The protein exists in plasma as a tetramer comprised of two A subunits and two B subunits. Each subunit has a molecular weight of 83,000 Da, and the complete protein has a molecular weight of approximately 330,000 Da. Factor XIII catalyzes the cross-linkage between the γ-glutamyl and ε-lysyl groups of different fibrin strands. The catalytic activity of factor XIII resides in the A subunits. The B subunits act as carriers for the A subunits in plasma factor XIII. Recombinant factor XIII can be produced according to the process described in European Patent No. 0 268 772 B1. The level of factor XIII in the plasma can be increased by administering a factor XIII concentrate, derived from human placenta or plasma, called FIBROGAMMIN® (Aventis Corp.) or by administration of recombinant factor XIII. When recombinant factor XIII is used, only the 'A$_2$'homodimer is generally administered without the 'B$_2$' subunit.

Administration of factor XIII to a subject is generally done intravenously. When administering therapeutic proteins by injection, the administration may be by continuous infusion or by single or multiple boluses. A pharmaceutical composition comprising factor XIII can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. A suitable pharmaceutical composition of factor XIII will contain 1 mM EDTA, 10 mM Glycine, 2% sucrose in water. An alternative formulation will be a factor XIII composition containing 20 mM histidine, 3% wt/volume sucrose, 2 mM glycine and 0.01% wt/vol. polysorbate, pH 8.

Other suitable carriers are well known to those in the art. See, for example, Gennaro (ed.), *Remington's Pharmaceutical Sciences,* 19th Edition (Mack Publishing Company 1995).

The levels of factor XIII in an individual can be determined by assays well known in the art such as the BERICHROM® F XIII assay (Dade Behring Marburgh GmbH, Marburg, Germany). The normal adult has an average of about 45 ml of plasma per kg of body weight. Each liter of blood has 1000 units (U) of factor XIII. The amount of factor XIII administered should be enough to bring an individual's level of factor XIII in the plasma to at least 100% of normal plasma or preferably 1–5% above normal. A dose of 0.45 U/kg would raise the level of factor XIII by about 1% compared to normal. One unit of factor XIII is about 10 μg of recombinant factor XIII, which contains only the dimerized A subunit. Thus, to raise the level of factor XIII by 1%, one would administer about 4.5 μg of the A2 subunit per kilogram weight of the individual. So to raise the level 30% of normal, one would administer 13.5 U/kg. For a 75 kg individual this would be about 1,012.5 U. Some patients may have consumptive coagulopathies that involve factor XIII losses. In such cases, a higher dosing (e.g., 1–2 U/kg-%) or multiple dosing of factor XIII (e.g., 1–2 U/kg-%-day) may be required.

What is claimed is:

1. A method for inhibiting coumarin anticoagulant-induced bleeding or hemorrhage in an individual comprising administering to the individual a therapeutically effective amount of a composition comprising factor XIII as the sole active agent.

2. The method of claim 1, wherein the anticoagulant is warfarin or dicoumarol.

3. The method of claim 1, wherein the factor XIII is recombinant human factor XIII.

4. A method for inhibiting coumarin anticoagulant-induced bleeding or hemorrhage in an individual comprising administering to the individual a therapeutically effective amount of a first composition comprising factor XIII as the sole active agent and a second composition comprising vitamin K.

5. The method of claim 4, wherein the factor XIII is recombinant human factor XIII.

6. The method of claim 3, wherein the composition is administered intravenously to the individual.

7. The method of claim 5, wherein the first composition is administered intravenously to the individual.

* * * * *